United States Patent
Mark et al.

(10) Patent No.: US 7,322,990 B1
(45) Date of Patent: Jan. 29, 2008

(54) NEEDLE GUIDE FOR STEREOTACTIC BIOPSY

(75) Inventors: Joseph L. Mark, Indianapolis, IN (US); Zachary R. Nicoson, Indianapolis, IN (US)

(73) Assignee: Suros Surgical Systems, Inc., Indianapolis, IN (US)

( * ) Notice: Subject to any disclaimer, the term of this patent is extended or adjusted under 35 U.S.C. 154(b) by 458 days.

(21) Appl. No.: 10/377,542

(22) Filed: Feb. 28, 2003

(51) Int. Cl.
  *A61B 19/00* (2006.01)
  *A61B 6/08* (2006.01)
  *A61B 1/00* (2006.01)
  *A61B 5/05* (2006.01)
  *A61B 8/14* (2006.01)
  *A61B 10/00* (2006.01)
  *H05G 1/00* (2006.01)

(52) U.S. Cl. .................. 606/130; 378/205; 378/208; 600/114; 600/417; 600/461; 600/462; 600/562; 600/567; 604/116

(58) Field of Classification Search ........ 600/564–568, 600/562, 461, 462; 606/130; 378/37, 205, 378/208; 128/915, 916; 604/424, 116; 248/674
See application file for complete search history.

(56) References Cited

U.S. PATENT DOCUMENTS

| | | | | |
|---|---|---|---|---|
| 3,070,052 A | * | 12/1962 | Freeman | 112/235 |
| 3,839,777 A | * | 10/1974 | Puzio | 269/55 |
| 4,402,324 A | * | 9/1983 | Lindgren et al. | 600/461 |
| 5,695,501 A | * | 12/1997 | Carol et al. | 606/130 |
| 6,602,203 B2 | * | 8/2003 | Stephens et al. | 600/566 |
| 6,612,990 B1 | * | 9/2003 | Pruter | 600/461 |
| 6,884,219 B1 | * | 4/2005 | Pruter | 600/459 |

\* cited by examiner

*Primary Examiner*—(Jackie) Tan-Uyen Ho
*Assistant Examiner*—Melissa Ryckman
(74) *Attorney, Agent, or Firm*—Rader, Fishman & Grauer, PLLC

(57) ABSTRACT

In a biopsy system having a biopsy needle guide secured to a needle guide support bracket, a biopsy needle guide is provided that includes a body having a periphery that defines an edge of the needle guide, the periphery defining a top surface, a bottom surface and a pair of side surfaces. A cradling aperture is positioned in the body and sized to engage the needle guide support bracket. A channel is provided in communication with the cradling aperture. The channel extends inwardly from one of the side surfaces of the body toward the cradling aperture. The needle guide of the present invention inhibits movement of the needle guide relative to the support bracket during a biopsy procedure.

37 Claims, 4 Drawing Sheets

NEEDLE GUIDE FOR STEREOTACTIC BIOPSY

BACKGROUND OF THE INVENTION

1. Field of the Invention

The present invention relates generally to stereotactic breast biopsy systems and more particularly to a needle guide suitable for use in a stereotactic breast biopsy system to guide insertion of a biopsy needle into a patient.

2. Description of the Related Art

Stereotactic breast biopsy systems are a precise, minimally invasive diagnostic tool for use in performing fine-needle aspiration and needle core biopsies of the human breast to determine whether a breast lesion is benign or malignant. Needle biopsies, unlike more invasive surgical procedures, are typically performed on an out-patient basis with local anesthesia. Stereotactic breast biopsy systems generally include an ergonomically contoured table that comfortably supports the patient in a stable, fixed position that exposes the patient's breast. Stereotactic breast biopsy systems also generally include a diagnostic imaging system for targeting the lesion to be biopsied. The location of the target lesion is used by a guidance system to guide insertion of the biopsy needle into the patient's breast tissue.

The biopsy needle used in a stereotactic breast biopsy is typically a component of a biopsy gun, which is supported by the guidance system in an appropriate holder. The biopsy needle is relatively long requiring the holder to include a support bracket to reduce deflection of the biopsy needle during deployment and use. The support bracket typically includes a needle guide at a distal end thereof through which the biopsy needle passes. The needle guide minimizes non-axial movement or deflection of the biopsy needle during a biopsy to ensure that the biopsy needle is inserted into the correct location of the patient's breast adjacent the target lesion.

Typical biopsy needle guides include an upper support portion having a hole through which the biopsy needle extends and a lower attachment portion that is removably secured to a cylindrical pin on the support bracket. The lower attachment portion of the biopsy needle guide includes a pair of spaced apart, downwardly extending legs that define a generally circle-shaped void therebetween to accommodate the diameter of the support bracket pin once the components are secured together. Because the support bracket pin is larger than the space between the needle guide legs, the legs are deflectable laterally away from each other as the biopsy needle guide is assembled vertically onto the pin.

During operation of the stereotactic breast biopsy system described above, the biopsy gun is first placed in the appropriate holder. The coordinates of the lesion, as determined by the diagnostic imaging system, are dialed in and the needle tip is moved forward until the desired pre-deployment position of the holder is achieved. The holder and biopsy gun are then deployed causing the biopsy needle to be inserted into the patient's breast tissue. The deployment of the biopsy needle into the breast is typically instantaneous, as the biopsy gun holder is generally spring loaded or otherwise configured for rapid deployment.

Due to the density of the breast tissue, the forces imposed on the biopsy needle guide are not necessarily axial, i.e., along the axis of the biopsy needle. More particularly, the forces imposed on the needle guide are primary axial with a component of the force being perpendicular to the axis of the biopsy needle due to deflection of the biopsy needle entering the relatively dense breast tissue. In other words, a component of the deployment force is imposed on the needle guide in the vertical direction. When the vertical force imposed on the needle guide exceeds the resilient force of the needle guide legs around the support bracket pin, the needle guide can move relative to the support bracket, or becomes disengaged therefrom. The limitations specifically minimized and/or eliminated by the present invention include improper deployment of a biopsy needle due to movement of the biopsy needle guide relative to the support bracket.

SUMMARY OF THE INVENTION

In a stereotactic breast biopsy system having a biopsy needle guide secured to a needle guide support bracket, a biopsy needle guide is provided that includes a body having a periphery that defines an edge of the needle guide, the periphery defining a top surface, a bottom surface and a pair of side surfaces. A cradling aperture is positioned in the body and includes an inner surface sized to engage the needle guide support bracket. A channel is provided in communication with the cradling aperture. The channel extends inwardly from one of the side surfaces of the body toward the cradling aperture.

In an embodiment of the present invention, the cradling aperture and the channel define first and second legs that surround a portion of the support bracket pin. When the needle guide is assembled onto the support bracket, one of the legs of the needle guide wraps around a lower portion of support bracket pin. Because of this configuration, a vertical force imposed on the needle guide during a biopsy procedure will not cause significant movement of the needle guide relative to the support bracket or otherwise cause it to become disengaged therefrom, unlike the prior art.

BRIEF DESCRIPTION OF THE DRAWINGS

The features and inventive aspects of the present invention will become more apparent upon reading the following detailed description, claims, and drawings, of which the following is a brief description:

DESCRIPTION OF THE PREFERRED EMBODIMENTS

Figure 1:
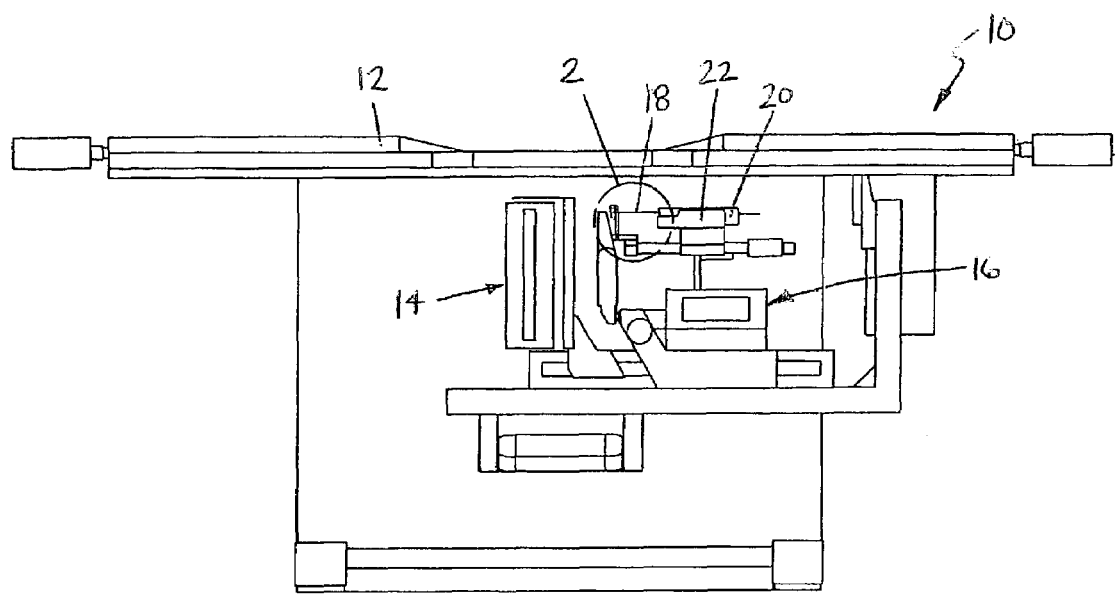
FIG. 1 is a simplified elevational view of an exemplary stereotactic breast biopsy system that employs the biopsy needle guide of the present invention.

Referring now to the drawings, preferred embodiments of the present invention are shown in detail. Referring to FIG.

1, there is shown a simplified illustration of an exemplary stereotactic breast biopsy system 10 for use in performing fine-needle aspiration and needle core biopsies of the human breast to determine whether a breast lesion is benign or malignant. Stereotactic breast biopsy system 10 includes an ergonomically contoured table 12 that comfortably supports the patient (not shown) in a stable, fixed position that exposes that patient's breast. Stereotactic breast biopsy system 12 also includes a diagnostic imaging system 14 for targeting the lesion to be biopsied. The location of the target lesion is used by a guidance system 16 to guide insertion of a biopsy needle 18 into the patient.

In the disclosed embodiment, the biopsy needle 18 is a component of a biopsy gun 20 that is supported by the guidance system 16 in an appropriate holder 22. An exemplary biopsy gun for use in stereotactic breast biopsy system 10 is the biopsy device marketed by Suros Surgical Systems, Inc. of Indianapolis, Ind. under the name ATEC™ (Automated Tissue Excision and Collection).

Biopsy needle 18 is relatively long requiring the holder 22 to include a support bracket 24 to reduce deflection of the biopsy needle 18 during deployment and use. The support bracket 24, which is attached to guidance system 16 using a movable L-shaped flange 26, includes a needle guide 28 through which biopsy needle 18 extends. To accommodate the diameters of various biopsy needles 18, the needle guide 26 is removably affixed to support bracket 24.

Figure 2:
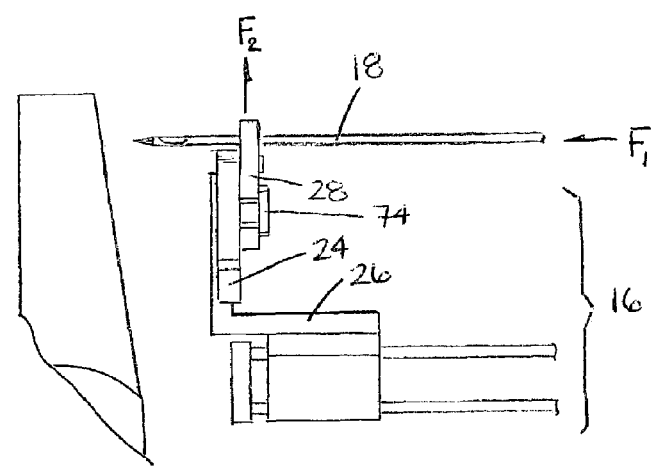
FIG. 2 is an enlarged detail view of a portion of the stereotactic breast biopsy system illustrated in FIG. 1.

Holder 22 is spring-loaded or otherwise configured so that biopsy needle 18 is rapidly deployed into the patient's breast tissue. Rapid deployment of biopsy needle 18 into the breast tissue reduces the tendency of biopsy needle 18 to deflect due to dense breast tissue. The deployment forces imposed on biopsy needle 18 and needle guide 28 are generally represented in FIG. 2 by force vectors $F_1$ and $F_2$. During deployment, holder 22 generates primarily an axial force $F_1$ along the axis of biopsy needle 18 to insert biopsy needle 18 into the patient's breast tissue. Depending on the tissue's density or resistance to entry of biopsy needle 18, a weaker vertical force $F_2$ may be imposed on needle guide 28 as biopsy needle 18 is deflected against needle guide 28.

Figure 3:
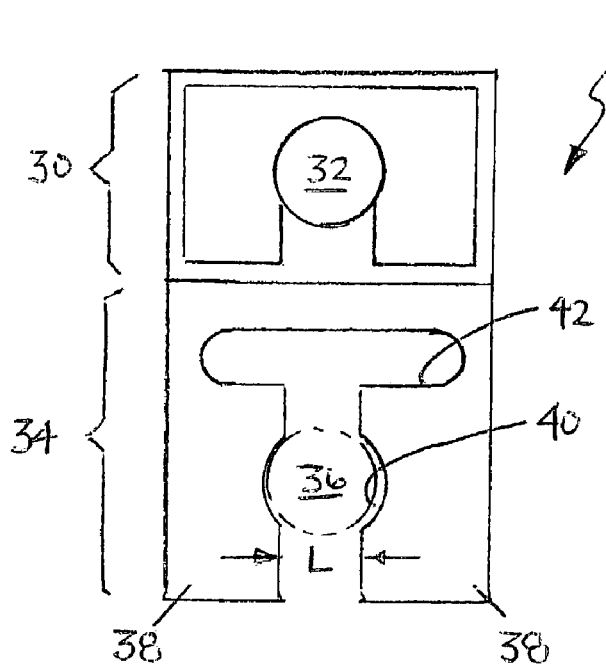
FIG. 3 is a front elevational view of a prior art biopsy needle guide.

The prior art biopsy needle guide 28' is depicted in FIG. 3. The prior art needle guide 28' includes an upper support portion 30 having a hole 32 through which biopsy needle 18 extends, and a lower attachment portion 34 that is removably secured to a pin 36 (shown in phantom) on support bracket 24. The lower attachment portion 34 of biopsy needle guide 28' includes a pair of spaced apart, downwardly extending legs 38 that define a generally circular-shaped void 40 therebetween to accommodate the diameter of support bracket pin 36 once the components are secured together.

Because the diameter of support bracket pin 36 is larger than the separation L between needle guide legs 38, the legs 38 are deflectable laterally away from each other as biopsy needle guide 28' is assembled vertically onto pin 36. To facilitate lateral deflection of legs 38, a T-shaped channel 42 is disposed between legs 38.

Once needle guide 28' is pushed onto support bracket pin 36, the resiliency of legs 38 function to hold needle guide 28' on support bracket pin 36. However, a sufficient vertical force $F_2$ imposed on needle guide 28' may overcome the resilient forces of legs 38 causing legs 38 to deflect outwardly and allow needle guide 28' to move or become disengaged from support bracket 24. The resulting movement of needle guide 28' would facilitate deployment of biopsy needle 18 to an incorrect location in the patient's breast tissue.

Figure 4:
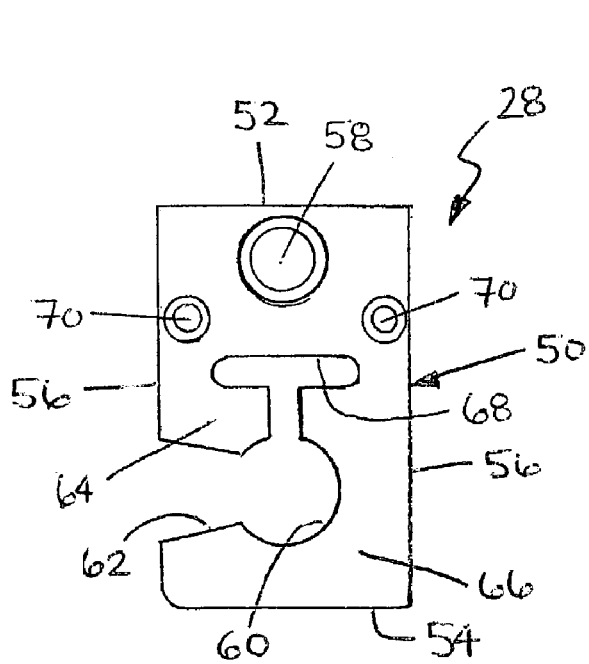
FIG. 4 is a front elevational view of a biopsy needle guide according to an embodiment of the present invention.
Figure 5:
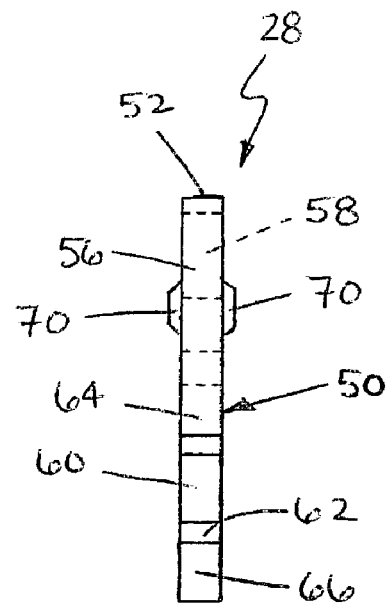
FIG. 5 is a side elevational view of the biopsy needle guide of FIG. 4.

Improper deployment of biopsy needle 18 due to movement of biopsy needle guide 28 relative to support bracket 24 is overcome by the present invention. Particularly, FIGS. 4 and 5 illustrate a biopsy needle guide 28 according to an embodiment of the present invention. Needle guide 28, which is made of a strong, yet resilient material, such as plastic, includes a body 50 having a periphery that defines an edge of needle guide 28. The periphery of needle guide 28 includes a top surface 52, a bottom surface 54 and a pair of side surfaces 56.

Body 50 also includes a hole 58 through which biopsy needle 18 extends. At least one face of body 50 surrounding hole 58 is preferably countersunk to facilitate alignment of biopsy needle 18 with hole 58 as it passes through.

Body 50 is also provided with a cradling aperture 60, an inner surface of which is sized to engage support bracket pin 36 to secure needle guide 28 to support bracket 24. A channel 62 is provided in communication with cradling aperture 60, as it extends inwardly from one of the side surfaces 56 of body 50 toward cradling aperture 60. Channel 62 tapers inwardly as it extends from side surface 56 into cradling aperture 60.

Cradling aperture 60 and channel 62 together define first and second legs 64 and 66, respectively. A distal end of first leg 64 is defined in part by an upper tapered surface of channel 62 and in part by the inner surface of cradling aperture 60. A distal end of second leg 66 is defined by a lower tapered surface of channel 62. The remainder of second leg 66 is defined at its lower extreme by bottom surface 54, at its outer extreme by side surface 56 and at its inner extreme by the inner surface of cradling aperture 60. In the disclosed embodiment, second leg 66 is substantially J-shaped; however second leg 66 could also function having a substantially L-shaped profile. First and second legs 64, 66 are separated by a generally T-shaped channel 68 that facilitates deflection of first and second legs 64, 66 as needle guide 28 is secured to support bracket 24.

Body 50 is also provided with a pair of spaced apart positioning tabs 70, which inhibit rotation of biopsy needle guide 28 relative to support bracket 24 once it is secured thereto. In the disclosed embodiment, positioning tabs 70 are each defined by a tapered protrusion that extends outwardly from a face of body 50. Positioning tabs 70 are preferably positioned on each face of body 50 so that needle guide 28 can be installed on support bracket 24 in either direction. Alternatively, a single positioning tab 70 could be included on each face of body 50.

Figure 7:
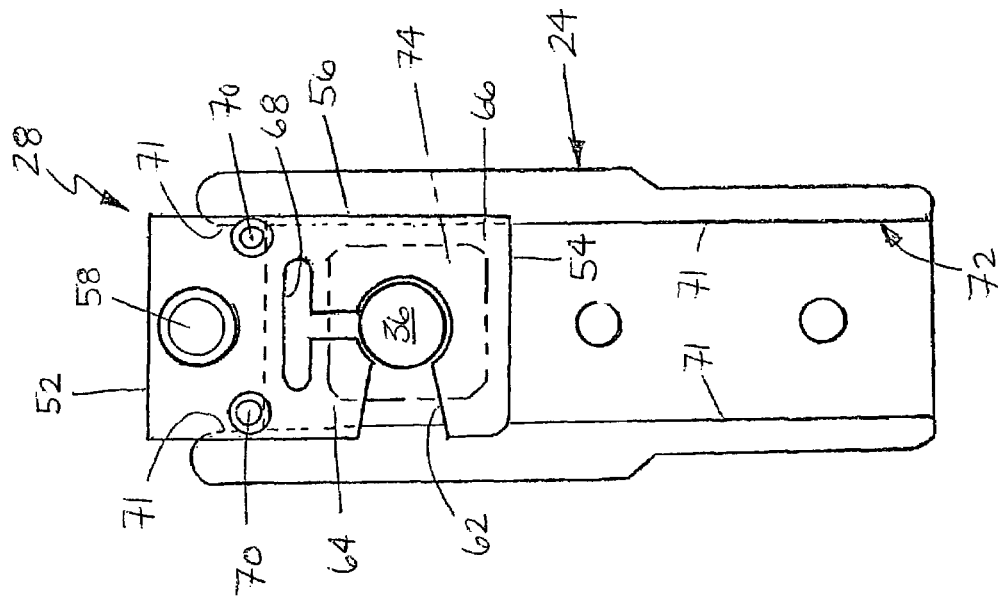
FIG. 7 is a front elevational view of the biopsy needle guide of the present invention after assembly onto the support bracket of the stereotactic breast biopsy system.
Figure 6:
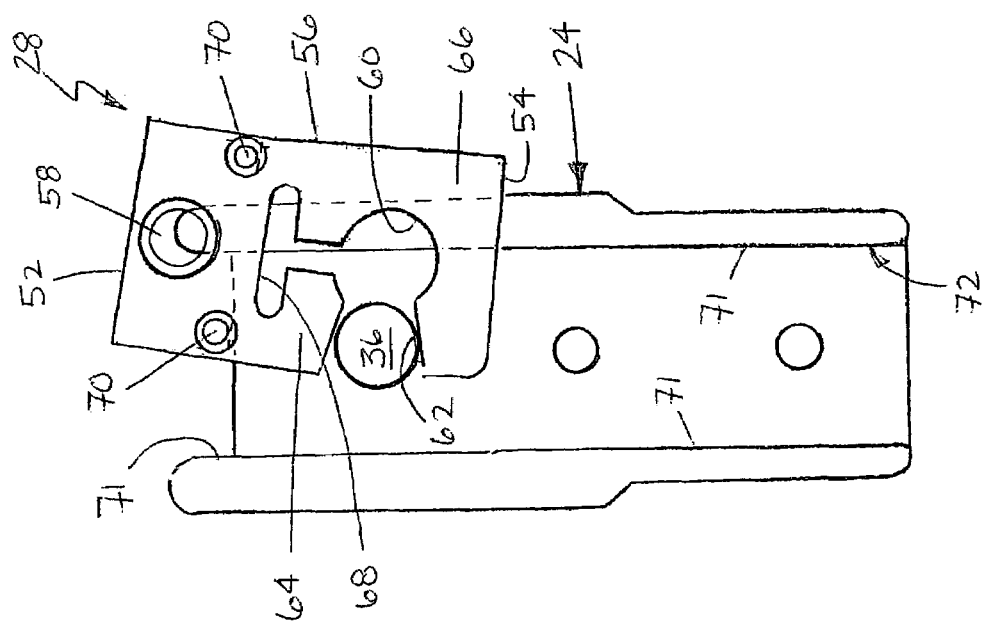
FIG. 6 is a front elevational view of the biopsy needle guide of the present invention during assembly onto a support bracket of the stereotactic breast biopsy system.

Referring to FIGS. 6 and 7, needle guide 28 is secured to support bracket 24 by pushing first and second legs 64, 66 over support bracket pin 36. As shown in FIG. 6, support bracket pin 36 engages the upper and lower walls of channel 62 forcing legs 64 and 66 to deflect away from each other. As needle guide 28 is further pushed onto support bracket pin 36, first and second legs 64, 66 further deflect until support bracket pin 36 is received in cradling aperture 60. Once support bracket pin 36 is received in cradling aperture 60, first and second legs 64, 66 resiliently return to their pre-deflected position (FIG. 7) to cradle support bracket pin 36 therebetween.

Additionally, once support bracket pin 36 is received in cradling aperture 60, needle guide 28 can be rotated, if needed, to align positioning tabs 70 between opposing side walls 71 of a groove 72 disposed through the length of support bracket 24. Once aligned, positioning tabs snap into groove 72 and engage side walls 71 to inhibit rotation of needle guide 28 relative to support bracket 24.

Figure 8:
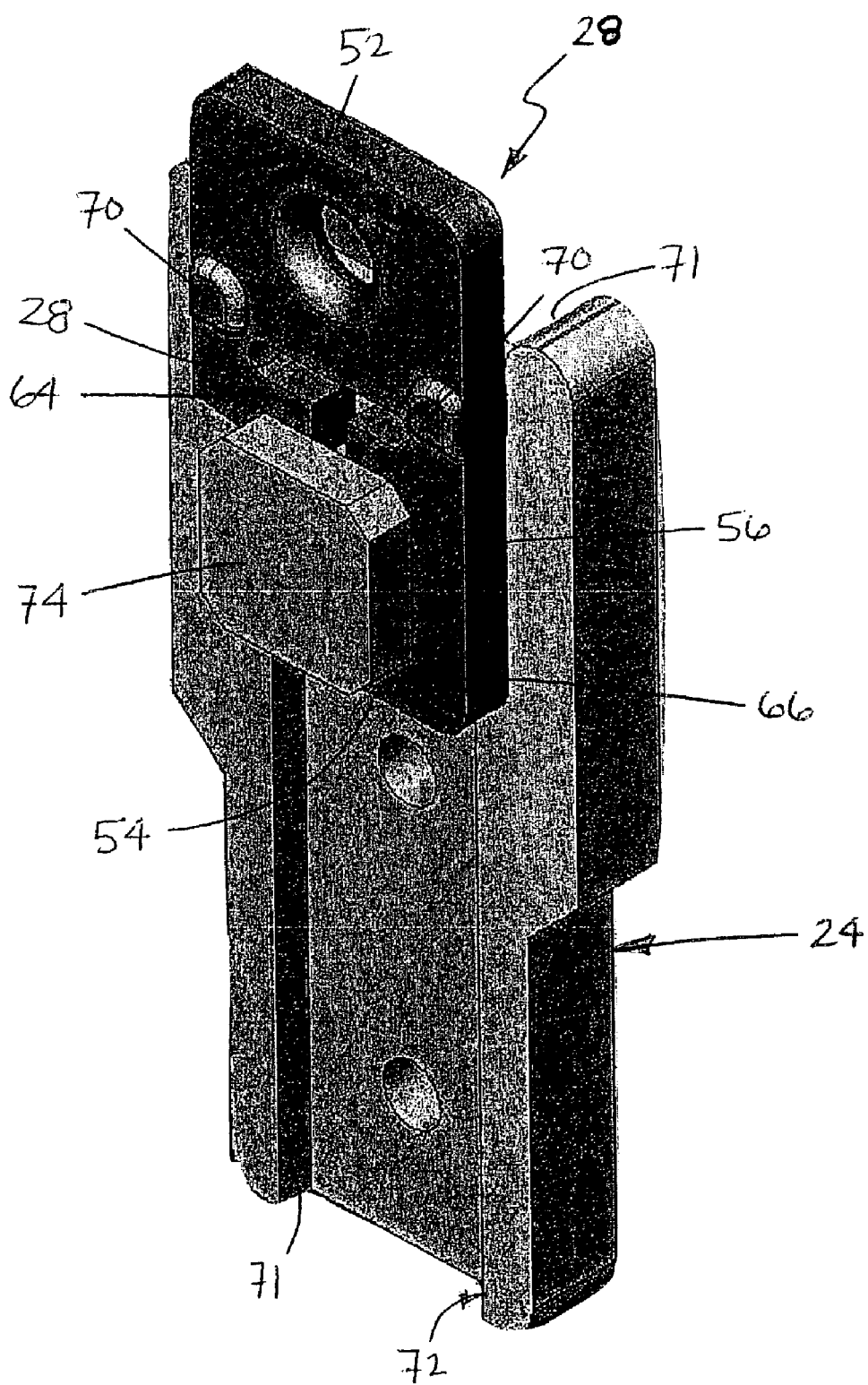
FIG. 8 is a perspective view of the biopsy needle guide of the present invention secured to the support bracket of the stereotactic breast biopsy system.

Referring to FIG. 8, a perspective view illustrating needle guide 28 and support bracket 24 in the assembled configuration is shown. Support bracket pin 36 includes an enlarged head 74 (shown in phantom in FIG. 7), which inhibits lateral movement of needle guide 28 relative to support bracket 24 along the axis of biopsy needle 18.

Once assembled, leg 66 wraps around the lower portion of support bracket pin 36. To remove needle guide 28 from support bracket 24, needle guide 28 must be slightly rotated and pulled in a direction generally perpendicular to side surface 56, causing support bracket pin 36 to exit cradling aperture 60 through channel 62. Because of this configuration, a significant vertical force $F_2$ will not cause needle guide 28 to significantly move relative to support bracket pin 36 or become disengaged therefrom, unlike the prior art.

Although certain preferred embodiments of the present invention have been described, the invention is not limited to the illustrations described and shown herein, which are deemed to be merely illustrative of the best modes of carrying out the invention. A person of ordinary skill in the art will realize that certain modifications and variations will come within the teachings of this invention and that such variations and modifications are within its spirit and the scope as defined by the claims.

What is claimed is:

1. In a biopsy system having a biopsy needle guide secured to a needle guide support bracket, the biopsy needle guide system comprising:
    a needle guide support bracket;
    a body having a periphery that defines an edge of the needle guide, the periphery defining a top surface, a bottom surface and a pair of side surfaces;
    a cradling aperture positioned in the body and sized to engage the needle guide support bracket;
    a tapered channel in communication with the cradling aperture, the channel extending inwardly from one of the side surfaces of the body toward the cradling aperture; and
    a biopsy needle aperture wherein a biopsy needle may extend therethrough, and wherein the needle aperture and the cradling aperture define a vertical axis through the needle aperture and the cradling aperture, and the channel extends inwardly from one of the side surfaces towards the vertical axis.

2. The biopsy needle guide of claim 1, wherein the body includes at least one positioning tab to inhibit rotation of the biopsy needle guide relative to the needle guide support bracket.

3. The biopsy needle guide of claim 2, wherein the body includes a pair of positioning tabs.

4. The biopsy needle guide of claim 1, wherein the body includes first and second legs.

5. The biopsy needle guide of claim 4, wherein a distal end of the first leg is defined in part by an upper surface of the channel.

6. The biopsy needle guide of claim 4, wherein a distal end of the second leg is defined by a lower surface of the channel.

7. The biopsy needle guide of claim 4, wherein one of the first and second legs is substantially J-shaped.

8. In a biopsy system having a biopsy needle guide secured to a needle guide support bracket, the biopsy needle guide system comprising:
    a needle guide support bracket;
    a body that includes a cradling aperture sized to engage the needle guide support bracket and a channel in communication with the cradling aperture, the channel extending inwardly from a periphery of the body toward the cradling aperture; and
    wherein the body further includes first and second legs defined in part by the cradling aperture, the first leg being shorter than the second leg, the cradling aperture has a width, the channel has a deflected condition defining a deflected width and an undeflected condition defining an undeflected width, and when the channel is in the undeflected condition, the undeflected channel width is less than the cradling aperture width, the biopsy needle guide further comprising a biopsy needle aperture wherein a biopsy needle may extend therethrough, and wherein the needle aperture and the cradling aperture define a vertical axis through the needle aperture and the cradling aperture, and the channel extends inwardly from a periphery of the body towards the vertical axis.

9. The biopsy needle guide of claim 8, wherein a distal end of the first leg is defined in part by an upper surface of the channel.

10. The biopsy needle guide of claim 8, wherein a distal end of the second leg is defined by a lower surface of the channel.

11. The biopsy needle guide of claim 8, wherein the second leg is substantially J-shaped.

12. The biopsy needle guide of claim 8, wherein the body includes at least one positioning tab to inhibit rotation of the biopsy needle guide relative to the needle guide support bracket.

13. The biopsy needle guide of claim 12, wherein the body includes a pair of positioning tabs.

14. The biopsy needle guide of claim 1, wherein said needle aperture is configured to allow rotation of said biopsy needle.

15. The biopsy needle guide of claim 8, wherein said needle aperture is configured to allow rotation of said biopsy needle.

16. In a biopsy system having a biopsy needle guide secured to a needle guide support bracket, the biopsy needle guide system comprising:
    a needle guide support bracket;
    a body having a periphery that defines an edge of the needle guide, the periphery defining a top surface, a bottom surface, and a pair of side surfaces;
    a cradling aperture positioned in the body and sized to engage the needle support bracket;
    a channel in communication with the cradling aperture, wherein the channel extends inwardly from one of the side surfaces of the body toward the cradling aperture, the channel and the cradling aperture define first and second legs, and at least one of the first and second legs is resilient; and
    a biopsy needle aperture wherein a biopsy needle may extend therethrough, and wherein the needle aperture and the cradling aperture define a vertical axis through the needle aperture and the cradling aperture, and the channel extends inwardly from one of the side surfaces towards the vertical axis.

17. The biopsy needle guide of claim 16, wherein the channel is tapered.

18. The biopsy needle guide of claim 16, wherein the channel and the aperture define an open area through the body.

19. The biopsy needle guide of claim 16, further comprising a generally t-shaped aperture in communication with the cradling aperture.

20. The biopsy needle guide of claim 16, wherein at least one of the first and second legs is resiliently displaceable in a direction away from the other of the first and second legs.

21. The biopsy needle guide of claim 1, wherein the channel and the cradling aperture define first and second legs, and at least one of the first and second legs is resilient.

22. The biopsy needle guide of claim 1, wherein at the channel and the cradling aperture define first and second legs, and at least one of the first and second legs is resiliently displaceable in a direction away from the other of the first and second legs.

23. The biopsy needle guide of claim 1, wherein the tapered channel and the cradling aperture define a open area through the body.

24. The biopsy needle guide of claim 8, wherein at least one of the first and second legs is resilient.

25. The biopsy needle guide of claim 8, wherein the channel is tapered.

26. The biopsy needle guide of claim 8, wherein the channel and the cradling aperture define an open area through the body.

27. The biopsy needle guide of claim 8, wherein at least one of the first and second legs is resiliently displaceable in a direction away from the other of the first and second legs.

28. A biopsy system, comprising:
the biopsy needle guide of claim 1; and
a biopsy needle disposed through the needle aperture.

29. In a biopsy system having a biopsy needle guide secured to a needle guide support bracket, the biopsy needle guide system comprising:
a needle guide support bracket;
a body having a periphery that defines an edge of the needle guide, the periphery defining a top surface, a bottom surface and a pair of side surfaces;
a cradling aperture positioned in the body and sized to engage the needle guide support bracket;
a tapered channel in communication with the cradling aperture, the channel extending inwardly from one of the side surfaces of the body toward the cradling aperture; and
a biopsy needle aperture wherein a biopsy needle may extend therethrough, and wherein the needle aperture defines an inner surface of the body, and the inner surface surrounds the needle aperture.

30. The biopsy needle guide of claim 29, wherein the needle aperture is a hole.

31. In a biopsy system having a biopsy needle guide secured to a needle guide support bracket, the needle guide system comprising:
a needle guide support bracket;
a body having a periphery that defines an edge of the needle guide, the periphery defining a top surface, a bottom surface and a pair of side surfaces;
a cradling aperture positioned in the body and sized to engage the needle guide support bracket;
a tapered channel in communication with the cradling aperture, the channel extending inwardly from one of the side surfaces of the body toward the cradling aperture, and
a needle hole wherein a biopsy needle may extend therethrough, and wherein the needle hole defines an inner surface of the body that does not intersect the top surface, bottom surface, or either side surface of the body, the body has a face, and a portion of the face surrounding the hole is countersunk.

32. In a biopsy system having a biopsy needle guide secured to a needle guide support bracket, the biopsy needle guide system comprising:
a needle guide support bracket;
a body that includes a cradling aperture sized to engage the needle guide support bracket and a channel in communication with the cradling aperture, the channel extending inwardly from a periphery of the body toward the cradling aperture; and
wherein the body further includes first and second legs defined in part by the cradling aperture, the first leg being shorter than the second leg, the cradling aperture has a width, the channel has a deflected condition defining a deflected width and an undeflected condition defining an undeflected width, and when the channel is in the undeflected condition, the undeflected channel width is less than the cradling aperture width, the biopsy needle guide further comprising a biopsy needle aperture wherein a biopsy needle may extend therethrough, and wherein the needle aperture defines an inner surface of the body that surrounds the needle aperture.

33. The biopsy needle guide of claim 32, wherein the needle aperture is a hole.

34. In a biopsy system having a biopsy needle guide secured to a needle guide support bracket, the biopsy needle guide system comprising:
a needle guide support bracket;
a body that includes a cradling aperture sized to engage the needle guide support bracket and a channel in communication with the cradling aperture, the channel extending inwardly from a periphery of the body toward the cradling aperture; and
wherein the body further includes first and second legs defined in part by the cradling aperture, the first leg being shorter than the second leg, the cradling aperture has a width, the channel has a deflected condition defining a deflected width and an undeflected condition defining an undeflected width, when the channel is in the undeflected condition, the undeflected channel width is less than the cradling aperture width, and the periphery of the body defines a top surface, a bottom surface, and a pair of side surfaces, the biopsy needle guide further comprising a needle hole wherein a biopsy needle may extend therethrough, and wherein the needle aperture defines an inner surface of the body that does not intersect the top surface, bottom surface, or either side surface of the body, the body has a face, and a portion of the face surrounding the hole is countersunk.

35. A biopsy system, comprising:
(a) a needle guide support bracket;
(b) a biopsy needle guide comprising a body that includes a cradling aperture sized to engage a needle guide support bracket, a channel in communication with the cradling aperture, the channel extending inwardly from a periphery of the body toward the cradling aperture, and first and second legs defined in part by the cradling aperture, the first leg being shorter than the second leg, wherein the cradling aperture has a width, the channel has a deflected condition defining a deflected width and an undeflected condition defining an undeflected width, and when the channel is in the undeflected condition, the undeflected channel width is less than the cradling aperture width, the biopsy needle guide further comprising a biopsy needle aperture wherein a biopsy needle may extend therethrough; and (c) a biopsy needle disposed through the needle aperture.

36. A method of performing a biopsy, comprising:

attaching the biopsy needle guide of claim 1 to the needle guide support bracket such that a portion of the needle guide support bracket is disposed in the cradling aperture; and deploying a biopsy needle through the needle aperture and into a patient's tissue.

37. A method of performing a biopsy, comprising:

providing a biopsy needle guide, the biopsy needle guide comprising a body that includes a cradling aperture sized to engage a needle guide support bracket, a channel in communication with the cradling aperture, the channel extending inwardly from a periphery of the body toward the cradling aperture, and first and second legs defined in part by the cradling aperture, the first leg being shorter than the second leg, and wherein the cradling aperture has a width, the channel has a deflected condition defining a deflected width and an undeflected condition defining an undeflected width, and when the channel is in the undeflected condition, the undeflected width is less than the cradling aperture width;

attaching the biopsy needle guide to a needle guide support bracket such that a portion of the needle guide support bracket is disposed in the cradling aperture, wherein the biopsy needle guide further comprises a needle aperture; and deploying a biopsy needle through the needle aperture and into a patient's tissue.

\* \* \* \* \*